United States Patent [19]

Tomlinson, Sr. et al.

[11] 4,414,227

[45] Nov. 8, 1983

[54] METHOD FOR REPELLING BIRDS, ESPECIALLY WOODPECKERS

[75] Inventors: Samuel J. Tomlinson, Sr.; Edward E. Dean; Leon M. Adams, all of San Antonio, Tex.

[73] Assignee: Southwest Research Institute, San Antonio, Tex.

[21] Appl. No.: 365,102

[22] Filed: Apr. 2, 1982

Related U.S. Application Data

[63] Continuation of Ser. No. 171,152, Jul. 22, 1980, abandoned.

[51] Int. Cl.³ .............................................. A01N 35/00
[52] U.S. Cl. .................................................... 424/331
[58] Field of Search ........................................ 424/331

[56] References Cited

FOREIGN PATENT DOCUMENTS 2222013 10/1974 France .

*Primary Examiner*—Leonard Schenkman

[57] ABSTRACT

A method for repelling birds, especially woodpeckers from selected areas or surfaces which comprises applying isophorone to such areas or surfaces.

5 Claims, No Drawings

METHOD FOR REPELLING BIRDS, ESPECIALLY WOODPECKERS

This is a continuation, of application Ser. No. 171,152, filed July 22, 1980 now abandoned.

This invention relates to a method for repelling birds, especially woodpeckers, from certain selected areas or surfaces. In one of its more specific aspects, it relates to a method for reducing or preventing damage to wooden utility poles and the like by woodpeckers.

Woodpecker damage to wooden poles and cross-arms has plagued the utility industry for many years. Not only is the damage costly, but the holes in the poles cause a weakening effect and also make them dangerous for linemen to climb. The extent of this damage is more widespread than is commonly realized and it has been estimated that the chiselling damage done by woodpeckers is more costly than that caused by wind, lightning, and icestorms combined. The seriousness of the problem of woodpecker damage is a long standing one and the literature contains many reports on stratagems for which utility companies have spent very substantial sums in an effort to solve this problem. Among these are:

1. Lashing the holed section of old poles to the tops of new poles or letting old poles stand lashed to the new poles. The theory underlying this was that the birds would prefer the older wood to the new freshly creosoted wood. The birds did not agree.

2. Tacking red flannel streamers and vaned metal strips to the poles. This repelled the birds briefly, apparently until they assured themselves these devices were harmless.

3. Wrapping the poles with hardware mesh cloth or with various sheetings such as plastic sheeting. This was largely ineffective in that the woodpeckers simply tore large holes in the hardware cloth to get at the wood. Wrapping the poles with other materials failed for a similar reason.

4. Applying chemical repellents.

It has long been desired to solve this problem by simply applying a chemical repellent to the poles which would cause the woodpeckers to avoid pecking on them. Hundreds of different chemicals have been reported to have been tried but none have been entirely successful for various reasons including inadequate repelling power or, if the repelling power was sufficient, failure to remain in place in effective amounts over extended periods of time.

In accordance with this invention, an area or surface from which birds are to be repelled has a chemical compound applied to it in an amount effective to repel the birds. The compound to be applied has the following formula:

wherein R is a methyl, ethyl or propyl group. The preferred chemical compound is isophorone which technically is 3,5, 5-trimethyl-2-cyclohexen-one-1. This specific compound corresponds to the general compound wherein the Rs are all methyl groups. Its physical properties are well known and it is readily available on the open market. While it is considered to be somewhat toxic to human beings, and contact with the skin and eyes is to be avoided, it is not considered a dangerous industrial hazard due to a low vapor pressure of about 0.2 millimeters at 20° C.

The repellent of this invention can be applied as a relatively pure compound, or in combination with a carrier or other inert materials. Solvents, emulsions or carriers can be used which are substantially inert with respect to the compound. Examples of solvent carriers which can be used, if desired, are various hydrocarbon fractions such as the naphthas. Since this ketonic material is only slightly soluble in water, it can be made up into an aqueous emulsion using suitable emulsifiers or wetting agents and the emulsion applied to the areas from which the birds are to be repelled. The compound can also be absorbed on suitable solid carriers, such as various clays, and applied as a dust, preferably with an adhesive to hold the carrier in place.

While the compound has a low vapor pressure and enjoys a substantial effective life even when applied so as to be continuously exposed to the atmosphere, it may be advantageous to apply it in such a manner so as to be substantially isolated from the atmosphere to further increase its effective life. One effective method of accomplishing this is to encapsulate the compound using techniques well known to the encapsulation art. The resulting capsules comprising discrete portions of the compound encased in insoluble impervious sheaths can be applied to a selected area or surface in any desired manner. For example, the capsules can be mixed with an adhesive or paint and applied to the surface to be protected. The compound is thus shielded from the atmosphere so that vaporization is substantially eliminated and the capsules can remain in place for long periods of time. However, an attack on such surface by a woodpecker or the like will cause at least some of the capsules to be ruptured thus releasing the compound for performing its repelling function.

The compound can also be applied in admixture with a suitable coating material, such as latex paint, which hardens to trap the compound within the hardened coating and to substantially isolate it from the atmosphere.

The amount of the ketonic compound to be applied should be sufficient to repel birds, especially woodpeckers, over an extended period of time. Since the compound has a very low volatility, it will remain in place over long periods of time during which it is effective in its repelling activity. The amount to be used can vary over a wide range depending on the manner of application, the desired period of its effectiveness and other factors. Usually an amount within the range of 0.5 and 3 ounces of the compound per square foot of surface is desirable. If the compound is encapsulated, the lower end of the range can be, for example, 0.1 ounce per square foot of surface. The high side of the range is usually dictated by economics.

EXAMPLE I

An aviary was constructed and two golden front adult woodpeckers were housed in it. A test pole (untreated) was placed in the aviary at the same time the birds were released therein so pecking and territory claims could be started. After a conditioning period of some six months, a new creosote impregnated distribution class electric power pole was placed in the aviary with one half of the top half of the pole painted with isophorone the other half was left unpainted. Approximately 100 cubic centimeters of the isophorone was used over a surface area of approximately 500 square centimeters. On the night of the original application, a heavy rainfall was received and two days later an additional 50 cc of isophorone was painted over the test area.

During the test period, the woodpeckers were fed with a feed ration consisting of live mealworms (worm, larvae and beetle), hen layer pellets and dog food pellets. The hen layer pellets and the dog food pellets were fed ad-lib and the mealworms were fed daily (50 to 100 each) on top of the ad-lib ration.

No activity was noticed on either side (treated or untreated) of the test pole until November. During the months of November through March, the untreated side of the test pole was vigorously attacked by the woodpeckers leaving numerous holes in same. During the same period, the treated side of the test pole was virtually unscathed and no damage was observed past the margin of the treated and untreated section of the pole.

Orientation preference was tested by rotating the poles by 90° and then 180°. No orientation was observed.

EXAMPLE II

The effect of isophorone on repelling an ordinary pen of chickens was observed by placing feed grain onto which isophorone has been sprayed until the grain was wetted in one tray and non-coated feed grain in another tray. The chickens readily ate the non-coated grain but would not eat the treated feed grain and no apparent ill affects were caused by the few pecks at the treated grain. It was observed that the avoidance appeared to be caused as the tongue came in contact with the treated grain.

We claim:

1. A method for repelling birds from a surface comprising selecting a surface from which it is desired to repel birds and applying to said surface a repelling amount of the compound of the formula

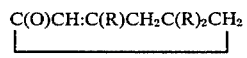

wherein R is a methyl, ethyl or propyl group.

2. The method of claim 1, wherein said compound is 3, 5, 5-trimethyl-2-cyclohexen-one-1.

3. The method as claimed in claims 1 or 2, wherein said compound is applied to said surface in encapsulated form.

4. The method of claim 3, wherein the encapsulated compound is applied with an adhesive or coating material to said surface.

5. The method of claim 4, wherein the coating material is paint.

* * * * *